(12) United States Patent
Carter et al.

(10) Patent No.: US 6,497,726 B1
(45) Date of Patent: Dec. 24, 2002

(54) MATERIALS AND METHODS FOR IMPROVED BONE TENDON BONE TRANSPLANTATION

(75) Inventors: Kevin C. Carter, Gainesville, FL (US); Michael Esch, Alachua, FL (US); Paul LaRochelle, Satelite Beach, FL (US)

(73) Assignee: Regeneration Technologies, Inc., Alachua, FL (US)

( * ) Notice: Subject to any disclaimer, the term of this patent is extended or adjusted under 35 U.S.C. 154(b) by 0 days.

(21) Appl. No.: 09/481,319

(22) Filed: Jan. 11, 2000

(51) Int. Cl.[7] ................................................. A61F 2/08
(52) U.S. Cl. .................................. 623/13.17; 623/13.11
(58) Field of Search .......................... 623/13.17, 13.11, 623/13.12, 13.14, 13.16, 13.18; 606/72, 73, 74

(56) References Cited

U.S. PATENT DOCUMENTS

| | | | |
|---|---|---|---|
| 4,927,421 A | * 5/1990 | Goble et al. | 606/73 |
| 5,062,843 A | 11/1991 | Mahony, III | |
| 5,139,520 A | 8/1992 | Rosenberg | |
| 5,282,802 A | 2/1994 | Mahony, III | |
| 5,320,115 A | 6/1994 | Kenna | |
| 5,366,457 A | 11/1994 | McGuire et al. | |
| 5,383,878 A | * 1/1995 | Roger et al. | 606/73 |
| 5,391,169 A | 2/1995 | McGuire | |
| 5,397,356 A | 3/1995 | Goble et al. | |
| 5,397,357 A | 3/1995 | Schmieding et al. | |
| 5,425,733 A | 6/1995 | Schmieding | |
| 5,425,767 A | * 6/1995 | Steininger et al. | 623/13.11 |
| 5,443,509 A | * 8/1995 | Boucher et al. | 623/16.11 |
| 5,454,811 A | 10/1995 | Huebner | |
| 5,496,326 A | 3/1996 | Johnson | |
| 5,681,314 A | 10/1997 | Derouin et al. | |
| 5,733,289 A | 3/1998 | Seedhom et al. | |
| 5,772,664 A | 6/1998 | DeSatnick et al. | |
| 5,897,570 A | 4/1999 | Palleva et al. | |
| 5,951,560 A | * 9/1999 | Simon et al. | 606/73 |
| 5,961,520 A | * 10/1999 | Beck, Jr. et al. | 606/72 |

* cited by examiner

Primary Examiner—Corrine McDermott
Assistant Examiner—Alvin Stewart
(74) Attorney, Agent, or Firm—McAndrews, Held & Malloy, Ltd.

(57) ABSTRACT

Disclosed herein is an improved Bone Tendon Bone graft for use in orthopedic surgical procedures. Specifically exemplified herein is a Bone Tendon Bone graft comprising one or more bone blocks having a groove cut into the surface therefor, wherein said groove is sufficient to accommodate fixation screw. Also disclosed is a method of harvesting grafts that has improved efficiency and increases the quantity of extracted tissue and minimizes time required by surgeon for implantation.

4 Claims, 6 Drawing Sheets

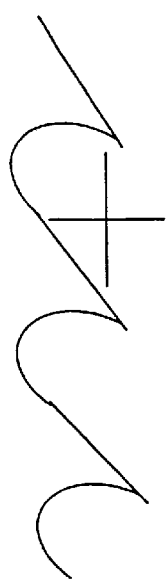
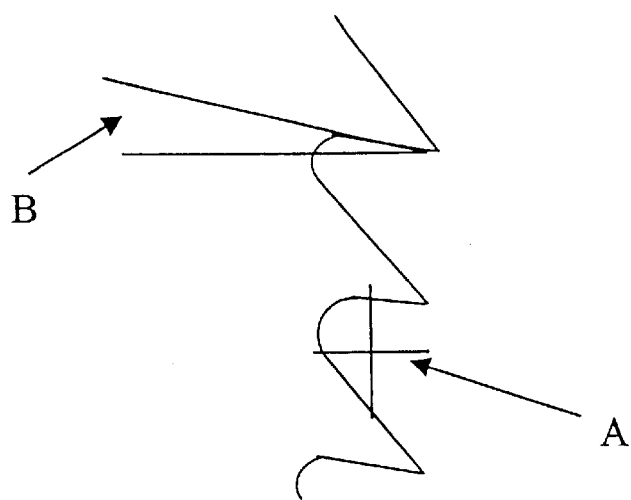
Figure 6A           Figure 6B
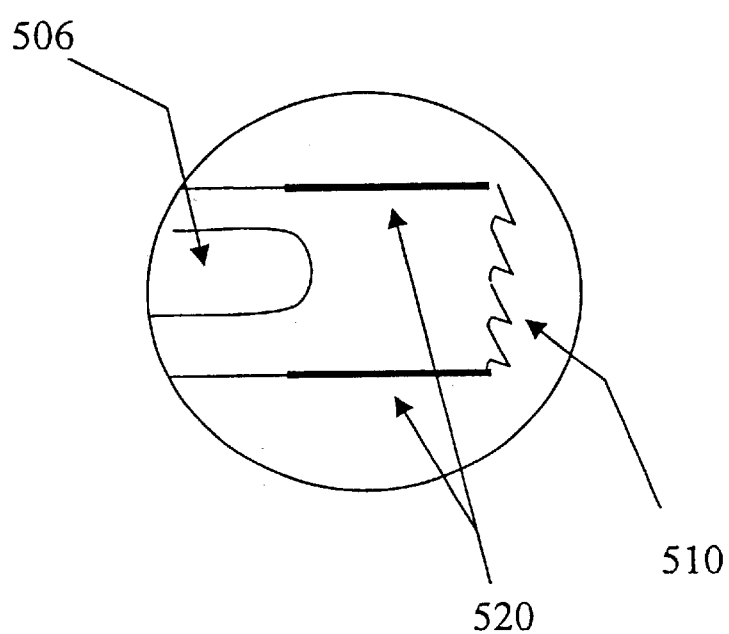
Figure 7

MATERIALS AND METHODS FOR IMPROVED BONE TENDON BONE TRANSPLANTATION

BACKGROUND OF THE INVENTION

Orthopedic medicine is increasingly becoming aware of the vast potential and advantages of using bone/tendon/bone grafts to repair common joint injuries, such as Anterior Cruciate Ligament (ACL) or Posterior Cruciate Ligament (PCL) tears. One technique that is currently used for repairing these types of injuries involves surgically reconnecting the torn portions of a damaged ligament. However, this technique is often not possible, especially when the damage to the ligament is extensive. To address situations where the damage to the joint ligaments is severe, another technique commonly performed involves redirecting tendons to provide increased support to a damaged knee. These conventional techniques are not without their shortcomings; in most cases, the repaired joint lacks flexibility and stability.

The recent utilization of bone/tendon grafts has dramatically improved the results of joint repair in cases of severe trauma. Even in cases of extensive damage to the joint ligaments, orthopedic surgeons have been able to achieve 100 percent range of motion and stability using donor bone/tendon grafts.

Despite these realized advantages, there have been some difficulties encountered with utilizing bone/tendon grafts. For example, surgical procedures involving transplantation and fixation of these grafts can be tedious and lengthy. Currently, bone/tendon/bone grafts must be specifically shaped for the recipient during surgery, which can require thirty minutes to over an hour of time. Further, surgeons must establish a means of attaching the graft, which also takes up valuable surgery time.

Another difficulty associated with using bone/tendon grafts is that there is a limited supply. This can result in a patient having to choose an inferior procedure simply based on the lack of availability of tissue. Accordingly, there is a need in the art for a system that addresses this and the foregoing concerns.

SUMMARY OF THE INVENTION

The subject invention concerns a novel bone tendon bone graft (BTB) that facilitates an easier and more efficient surgery for reconstructing ligaments in a joint. One aspect of the subject invention pertains to a BTB that comprises a tendon and two bone blocks positioned at opposite ends of the tendon, wherein the bone blocks are pre-shaped for uniform and consistent alignment into a recipient bone.

In a specific aspect, the subject invention pertains to a bone tendon bone graft useful in orthopedic surgery comprising one or more bone blocks, and a tendon attached to said one or more bone blocks; wherein said one or more bone blocks is cut to provide a groove sufficient to accommodate a fixation screw. Alternatively, the subject invention pertains to a bone tendon bone graft useful in orthopedic surgery comprising one or more bone blocks and a tendon attached to said one or more bone blocks, wherein said one or more bone blocks is pre-shaped into a dowel.

A further aspect of the subject invention pertains to a method of obtaining a plurality of bone tendon bone grafts comprising excising a first bone plug having attached thereto a tendon or ligament; and excising a second bone plug having attached thereto a tendon or ligament; wherein said first bone plug and said second bone plug are derived from contiguous bone stock and overlap such that excision of said first bone plug or said second bone plug forms a groove in the bone plug that is excised subsequent to the other.

In yet another aspect, the subject invention pertains to a method of conducting orthopedic surgery on a human or an animal comprising obtaining a bone tendon bone graft, said graft comprising a tendon or ligament having two ends, and one or more bone blocks attached to said tendon or ligament, wherein at least one of said one or more bone blocks has a groove suitable for accommodating a fixation screw.

An alternative aspect of the invention pertains to an implant comprising a bone block and a tendon, wherein the bone block comprises a groove for accommodating a fixation screw.

Yet a further aspect of the subject invention pertains to a BTB core cutter for harvesting BTB grafts in accordance with the principles of the subject invention.

These and other advantageous aspects of the subject invention are described in further detail below.

DETAILED DESCRIPTION OF THE DRAWINGS

FIG. 2 shows a side view of three different embodiments of BTBs in accordance with the subject invention.

FIG. 6A shows a close up view of a teeth configuration that is less desired for use with the subject invention.

FIG. 6B shows a close up view of a preferred embodiment of the teeth of the embodiment shown in FIG. 5.

FIG. 7 is a blown up view of the circled region as shown in FIG. 5.

DETAILED DISCLOSURE OF THE INVENTION

Figure 1:
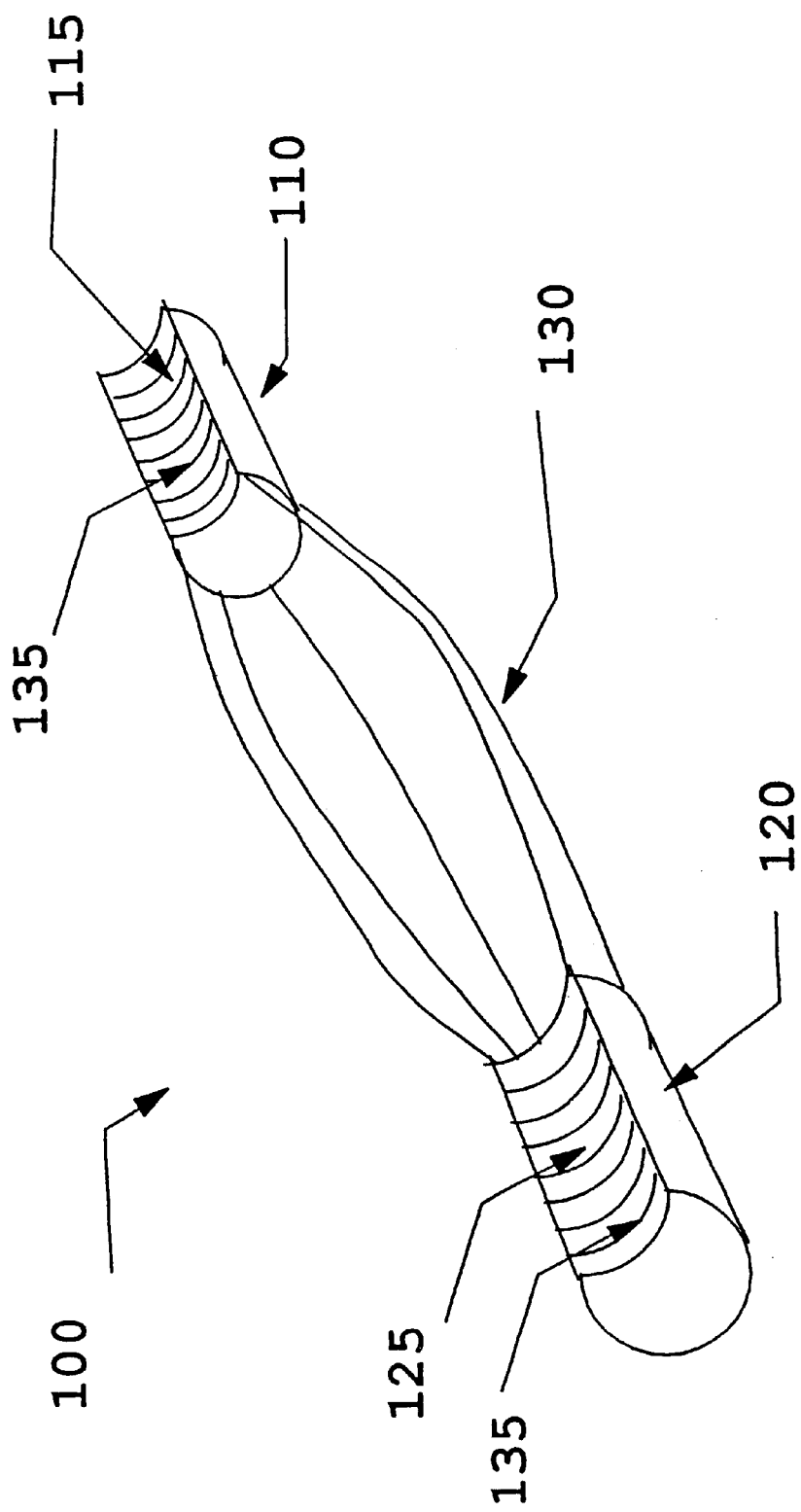
FIG. 1 shows an embodiment of a BTB having a groove with a thread profile disposed thereon.

Referring to FIG. 1, there is shown an embodiment directed to a BTB 100 comprising a first bone block 110 and a second bone block 120 interconnected by a tendon 130, wherein each bone block has been pre-shaped into dowels. The term "tendon" as used herein is intended in its broad sense and refers to fibrous connective tissue for use in grafts, such as, but not limited to, tendons, ligaments and demineralized bone. The terms "BTB" or "bone tendon bone graft" as used herein refer to a graft implant that comprises one or more tendon portions and one or more bone portions. The BTB is preferably isolated from the knee of a donor. However, in view of the teachings herein, those skilled in the art will readily appreciate that other areas of the body are suitable, albeit less preferred, for harvesting BTBs according to the subject invention, such as, but not limited to, the Achilles tendon/calcaneus region or shoulder region. In addition to BTBs having a tendon portion derived from naturally occurring tendon or ligament harvested from a donor, other examples of suitable implants would be readily appreciated by those skilled in the art, such as, but not limited to, segmentally demineralized bone (International Pub. No. WO/99/21515). In a more preferred embodiment, one of the bone blocks is derived from the patella while the other is derived from the end of the tibia, and the tendon is derived from the patellar tendon.

To facilitate placement of a fixation screw, the dowels are preferably machined down the length of the bone block to form radius cuts 115, 125. The radius cuts 115, 125 aid in the attachment of the graft to recipient bone because they provide a groove to position a fixation screw, which results in increased surface area at the contact between the bone block and the screw. The radius cuts 115, 125 provide the additional advantage of increasing the pull out loads of the bone block, as well as filling of "dead" space in the tunnel.

Fixation methods known in the art can be used in accord with the principles of the subject invention, which include, but are not limited to, staples, buttons, screw and washer, interference screws, and self-taping screws. In a preferred embodiment, fixation is accomplished by interference screws and/or self-taping screws. In an even more preferred embodiment, the radius cuts 115, 125 contain a thread profile 135 that matches the thread profile of the fixation screw, thereby further increasing the stability of fixation.

Figure 2A:
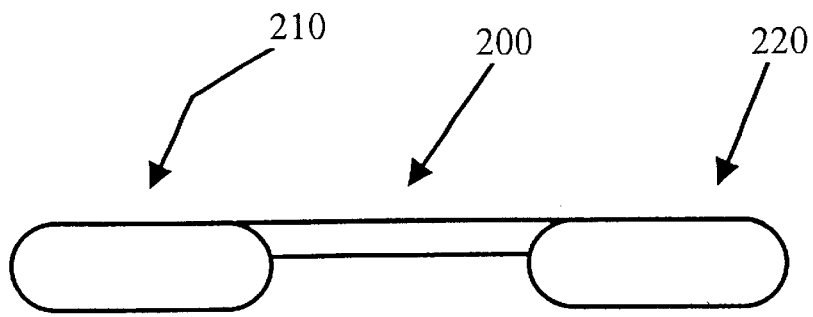
FIG. 2A shows an embodiment that comprises a basic configuration of the subject BTBs.
Figure 2B:
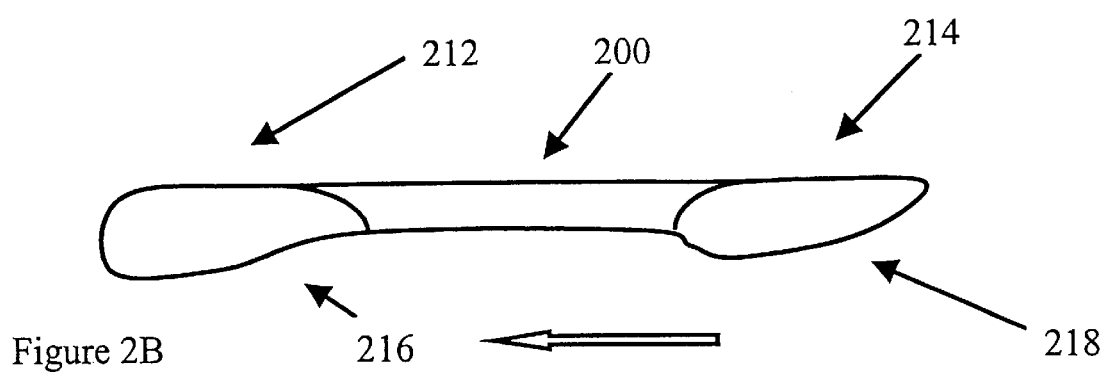
FIG. 2B shows another version of the BTB, wherein the bone blocks are preshaped into dowels with tapered ends.
Figure 2C:
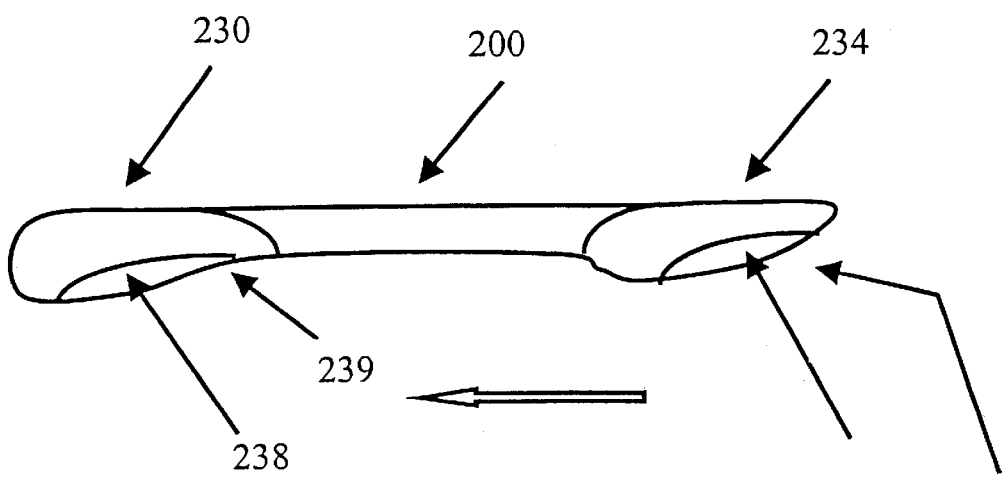
FIG. 2C illustrates a preferred version of the invention, which has a bone block with a proximal tapered region and a groove positioned on the bone block.

Referring now to FIG. 2, three different embodiments of the subject BTBs are shown. FIG. 2A shows an embodiment that comprises a basic configuration of the subject BTBs. Bone blocks 210 and 220 are in a pre-shaped dowel form with no groove thereon, and are connected by tendon 100. FIG. 2B shows another version of the BTB, wherein the bone blocks are preshaped into dowels with tapered ends. Bone block 212 is a dowel that has a proximal tapered region 216 in relation to tendon 200, and bone block 214 is preshaped into a dowel that has a distal tapered region 218 in relation to tendon 200. FIG. 2C illustrates a preferred version of the invention, which has a bone block 230 with a proximal tapered region 239 and a groove 238 positioned on the bone block 230. This version also comprises a second bone block 234 with a distal tapered region and a groove 236 positioned on bone block 234 as well. The embodiments shown in FIGS. 2B–C are tapered such that implantation into a pre-formed tunnel in recipient bone is preferred to occur in the direction of the arrow (see also FIG. 4).

Figure 3:
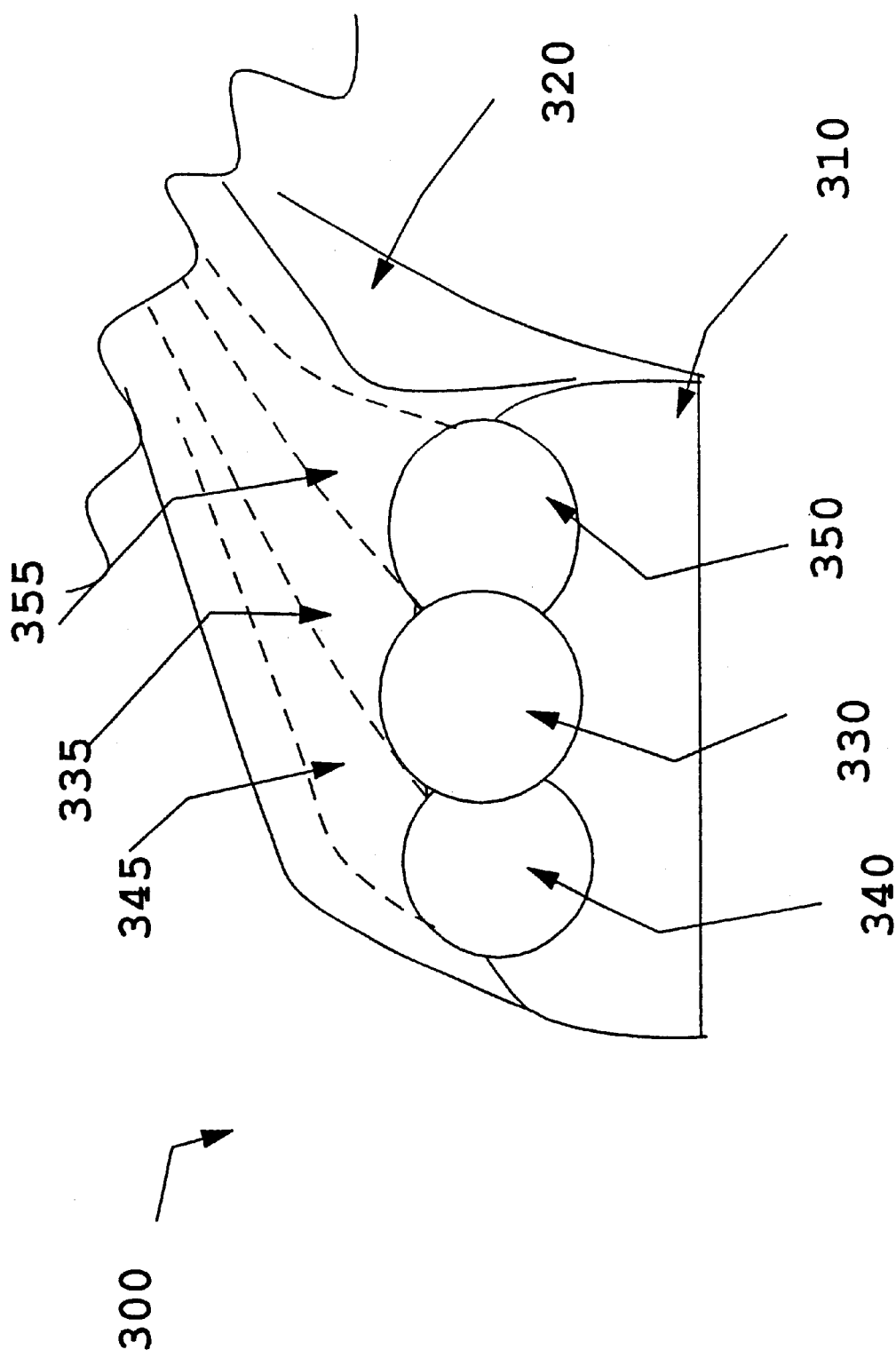
FIG. 3 depicts a frontal view of a donor area for harvesting BTBs in accordance with the teachings herein.

Referring to FIG. 3, an illustration of a donor area 300 is depicted, wherein three separate grafts 335, 345, and 355 are harvested. As shown, the three different grafts individually have at least one bone block 330, 340, and 350. While the sequence of harvesting the grafts is not critical, preferably, graft 335 is excised first, followed by excision of the outside grafts 345, 355. Excising graft 335 first results in the automatic cut in the other donor areas, thereby producing a groove in the bone blocks 340, 350 of the other grafts upon excision. In a preferred embodiment, the donor area is located at the top of the Tibia at the insertion of the patellar tendon 320. In an even more preferred embodiment, the donor area extends the length of the patellar tendon to the patella, wherein bone blocks are excised from the patella.

The bone blocks can be extracted with the use of conventional tools and protocols routinely practiced in the art, such as core cutter and hole saws. In a preferred embodiment, the bone blocks can be extracted through the use of a BTB bone cutter according to the teachings further described below.

The extracted bone blocks 330, 340, and 350 are generally shaped like a plug or dowel and are preferably further shaped by machining through conventional methods known in the art. In a specific embodiment the dowel is machined into dimensions suitable for various surgical procedures. The machining is preferably conducted on a graduated die, a grinding wheel, a lathe, or machining tools may be specifically designed and adapted for this purpose in view of the teachings herein. Preferred dimensions for the dowels include 8 mm, 9 mm, 10 mm, 11 mm, and 12 mm in diameter. Reproducibility of the product dimensions is an important feature for the successful use of such grafts in the clinical setting.

Figure 4:
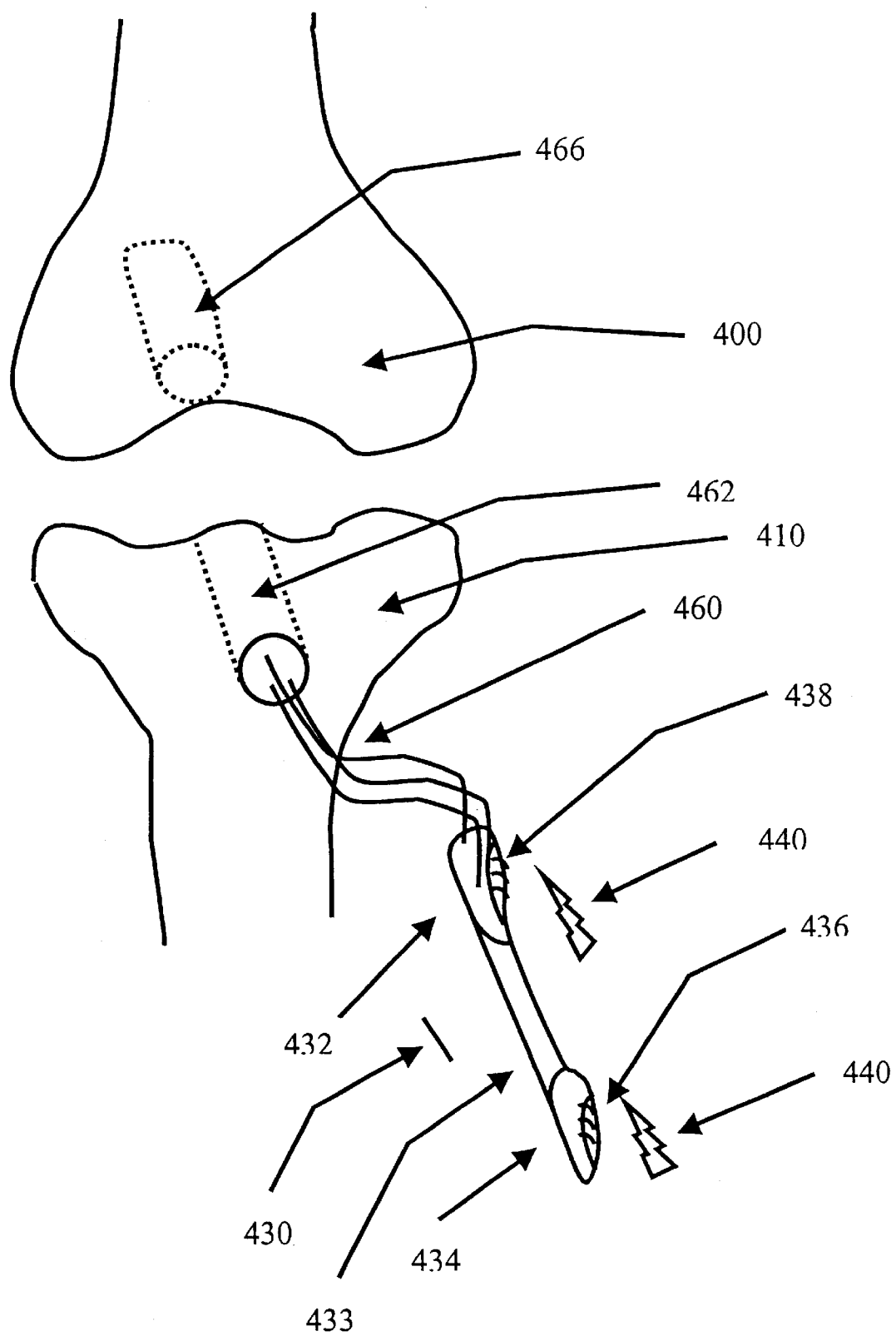
FIG. 4 is a depiction of another embodiment of the invention illustrating a reconstruction of an injured area through implantation of a BTB in accordance with the teachings herein.

In a specific embodiment, the subject invention is directed to a method of repairing an injured cruciate ligament in the knee involving the implantation of a BTB. FIG. 4 illustrates this procedure, and shows a femur 400 and tibia 410 having tunnels formed therein, 466 and 462, respectively, for receiving BTB 430, which comprises two bone blocks 432 and 434 connected by tendon 433. To aid in guiding the BTB 430 through tunnel 462, sutures 460 are optionally engaged to bone block 432, which allow a surgeon to pull the BTB 430 through tunnel 462 where the sutures 460 can then be removed. Once the BTB 430 is properly situated in tunnels 462 and 466, the BTB 430 is secured in the recipient bone by interference screws 440. The interference screws 440 are preferably self taping and are engaged by rotation in the space between grooves 438 and 436 and the inner walls of tunnels 466 and 462, respectively. In an even more preferred embodiment, the BTB can be pre-marked with alignment markings. Such markings can be positioned on the BTB to aid the surgeon in visualizing the depth of the BTB in the tunnels formed for receiving the BTB, as well as visualizing bone ligament junctions and rotation of the BTB.

Figure 5:
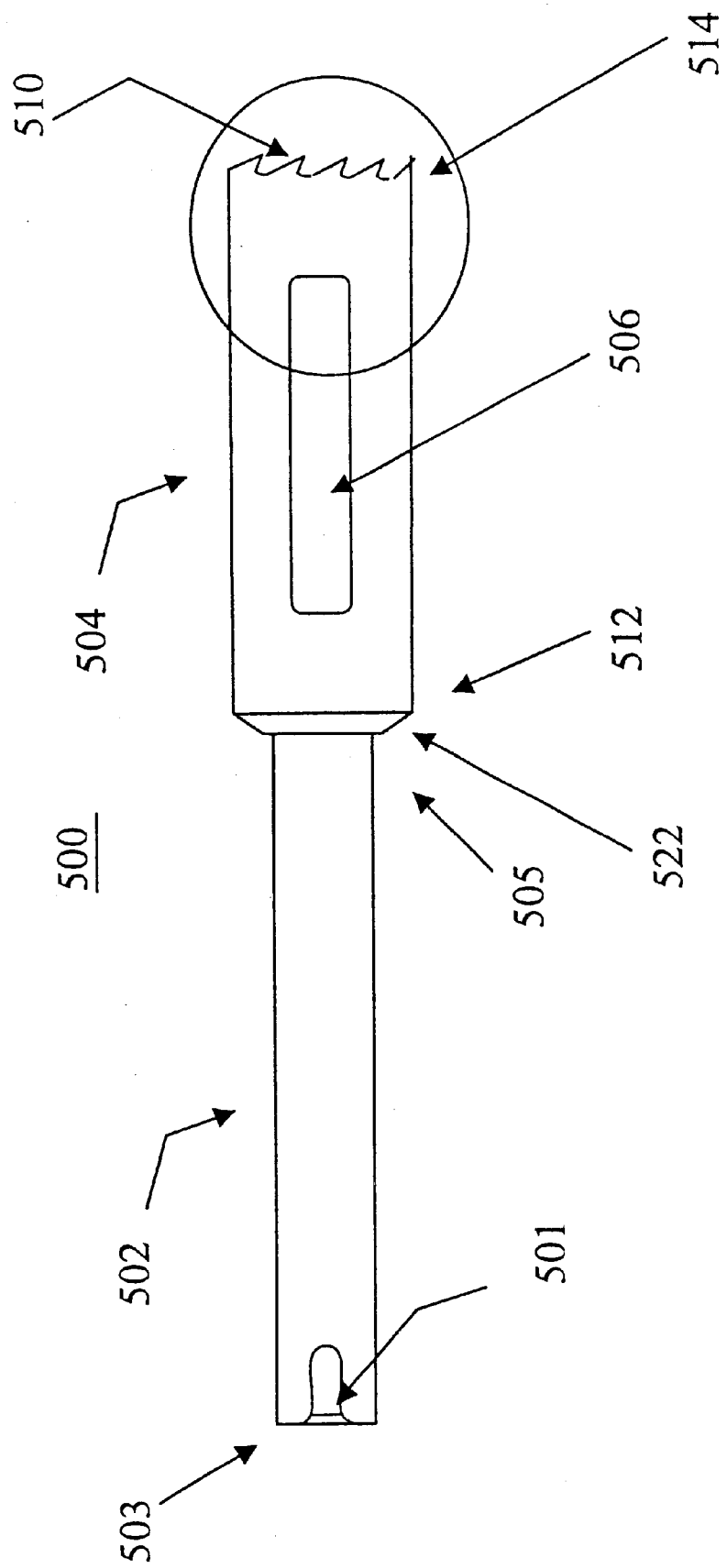
FIG. 5 shows a side view of a BTB core cutter of the subject invention designed for harvesting BTB grafts.

Referring now to FIGS. 5–7, another embodiment of the subject invention is shown that is directed to a BTB harvesting device, such as core cutter 500 that comprises a shaft 502 having a first end 503 and a second end 505. The first end 503 of the shaft 502 preferably has a cavity 501 longitudinally disposed thereon, which is designed for engaging a drill, such as by insertion of a Jacob's chuck attached to a power drill (e.g., Dupuy). The second end 505 of the shaft 502 can be attached to a first end 512 of a hollow cylinder 504. The second end 514 of the cylinder 504 preferably has teeth 510 disposed thereon. In a preferred embodiment the cylinder has at least one slot 506 disposed on its surface to aid in the removal of the cut graft tissue, from the core cutter 500. The slot 506 also provides a means to wash the graft during the extraction procedure to thereby decrease the chance of frictional burning of the graft. In a preferred embodiment, the shaft 502 is approximately 90 mm in length, the cylinder 504 is approximately 50 mm in length, and the slot 506 is approximately 30 mm in length. In an even more preferred embodiment, the first end of the hollow cylinder 512 has a chamfered portion 522 which angles down to the shaft 502.

A blown up view of the core cutter teeth 510 is illustrated in FIG. 6. It is preferred that the radius of the teeth A and rake angle of the teeth B ( also referred to as a bottom angle) are of appropriate values as to avoid failure (e.g. bending or breaking) of the teeth, as well as undesired damage to the graft. For example, FIG. 6A shows an unacceptable tooth pattern wherein the radius A and bottom angle B are too large, resulting in insufficient support structure for the tooth and inevitable failure. According to the subject invention, a core cutter having a diameter of approximately 10–11 mm preferably has approximately 14 teeth, with a tooth radius A of approximately 20–30 mm (25 mm being more preferred) and a bottom angle B of approximately 10–20 degrees (15 degrees being more preferred). For core cutters designed for smaller or larger bone blocks, the foregoing dimensions are preferably maintained, while the number of teeth are appropriately decreased or increased. In a preferred embodiment, the number of teeth are decreased or increased by two for every millimeter below or above, respectively, the 10–11 mm cylinder diameter. For example, a core cutter having a 12 mm cylinder diameter would preferably have about 16 teeth.

A blown up view of an end section (circle shown in FIG. 5) of the cylinder 504, is shown in FIG. 7, which illustrates a preferred embodiment of the cylinder 504 wherein the internal diameter (ID) is decreased slightly by adding a relief thickness 520 to the inner surface of the cylinder 504. This embodiment provides an additional convenience when using a size gauging device (e.g. ring) for selecting extracted bone blocks that are within desired parameters. For example, the selection of a BTB through a 10 mm sized gauging device would preferably require the BTB to be a slight fraction smaller in diameter than the gauging device, otherwise any insignificant irregularity in the shape of the BTB might cause it to fail to pass through the gauging device. The relief thickness 520 decreases the ID of the cylinder 504, thereby effectuating this slight modification to the BTB.

Those skilled in the art will appreciate that the graft may be an autograft, allograft, or xenograft. Xenograft implants may further require treatments to minimize the level of antigenic agents and/or potentially pathogenic agents present in the graft. Techniques now known, or those which are later developed, for preparing tissue such that it is suitable for and not rejected by the recipient are incorporated herein. In cases where the graft is an allograft or xenograft, a donor is preferably screened for a wide variety of communicable diseases and pathogens, including human immunodeficiency virus, cytomegalovirus hepatitis B, hepatitis C and several other pathogens. These tests may be conducted by any of a number of means conventional in the art, including, but not limited to, ELISA assays, PCR assays, or hemagglutination. Such testing follows the requirements of the following associations: (a) American Assocation of Tissue Banks. Technical Manual for Tissue Banking, Technical Manual-Musculoskeletal Tissues, pages M19–M20; (b) The Food and Drug Administration, Interim Rule, Federal Register, Vol. 58, No. 238, Tuesday, December 14, Rules and Regulations, 65517, D. Infectious Disease Testing and Donor Screening; (c) MMWR, Vol.43, No. RR-8, Guidelines for Preventing Transmission of Human Immunodeficiency Virus Through Transplantation of Human Tissue and Organs, pages 4–7; (d) Florida Administrative Weekly, Vol. 10, No.34, Aug. 21, 1992, 59A-1.001-014, 59A-1.005(12)(c), F.A.C., (12)(a)–(h), 59A-1.005(15, F.A.C., (4) (a)–(8). In addition to a battery of standard biochemical assays, the donor, or their next of kin can be interviewed to ascertain whether the donor engaged in any of a number of high risk behaviors such as having multiple sexual partners, suffering from hemophilia, engaging in intravenous drug use etc. Once a donor has been ascertained to be acceptable, the tissue for obtention of the BTBs as described above are recovered and cleaned.

The teachings of all patents and publications cited throughout this specification are incorporated by reference in their entirety to the extent not inconsistent with the teachings herein.

It should be understood that the examples and embodiments described herein are for illustrative purposes only and that various modifications or changes in light thereof will be suggested to persons skilled in the art and are to be included within the spirit and purview of this application and the scope of the appended claims.

EXAMPLE 1

Procedure for Harvesting of Crude BTB for Patellar Tendon Tibial Donor

A BTB was harvested according to the following procedure:

1. Using blunt and sharp dissection remove the three layers of connective tissue from the anterior portion of the tendon.
2. Using scalpel or scissors cut along the medial and lateral borders of the tendon. Use the scissors to bluntly dissect under the tendon to separate it from the fat layer.
3. Cut around the Patellar block to separate it form the proximal tibia and distal femur. Leave approximately 4 cm of quadriceps tendon attached to the patellar if required. If no quadriceps tendon attachment is specified then remove quadriceps from patellar completely using sharp dissection.
4. Pull tendon away from capsule and remove all excess adipose tissue to the point of tibial insertion.
5. With a saw make a transverse cut through approximately the tibial tuberosity about 30 mm from the tendon insertion point. Make a similar cut about 5 mm proximal to the insertion point, which will remove the tibial plateau.
6. With a saw, cut and square the sides of the tibia bone block even with the tendon.
7. With a saw cut and square the patella block on three sides (if quadriceps tendon is still attached square off only the medial and lateral sides).
8. Remove all extraneous soft tissue and cartilage from the patella, tibial tuberosity and tendon.
9. To hemisect the patellar tendon use a scalpel to divide the tendon into a medial half and a lateral half. Each half should be 14 mm or greater unless otherwise specified.
10. Using a saw, split the patella block and the tibia block in half following the same medial/lateral line used to split the tendon.
11. Thoroughly lavage the bone blocks with sterile water or saline.

EXAMPLE 2

Procedure for Forming Patellar Tendons with Preshaped Dowels for Patellar Tendon Tibial Donor A BTB was harvested according to the following procedure:

1. Using blunt and sharp dissection remove the three layers of connective tissue from the anterior portion of the tendon.
2. Using a scalpel or scissors cut along the medial and lateral borders of the tendon to separate it from the fat layer.
3. Cut around the Patellar block to separate it from the proximal tibia and distal femur.
4. Pull tendon away from capsule and remove all excess adipose tissue to the point of tibial insertion.
5. With a saw make a transverse cut through the tibial tuberosity about 30 mm from the tendon insertion point. Make a similar cut just proximal to the insertion point removing the tibial plateau. Make another cut across the coronal plane 20–30 mm posterior from the insertion point.

6. With a saw square the sides of the tibia bone block.
7. With a saw cut and square the patella block on the three sides.
8. Attach a vice to the tabletop. Place the tibia bone block in the vice so that it holds it along the proximal and distal sides. The distal side of the bone block should be facing the processor with the tendon going away from them. Tighten the vice so that it holds the bone securely but does not crush it.
9. Attach a Jacob's chuck to a drill and insert the appropriate size cutter. Tighten the chuck with the chuck key. Note: At least two plugs should be cut from each bone block.
10. Position the cutter against the bone block so the teeth of the cutter will skim just over the top of the tendon without catching the tendon. Position the cutter so that the maximum attachment is obtained throughout the length of the bone plug.
11. Turn drill on and begin drilling the plug. When the cutter nears the end of the plug, slow the drill until the cutter just breaks through the proximal end of the bone block. Remove the plug from the cutter and drill without damaging the tendon.
12. Repeat steps 10 and 11 for the second plug.
13. Using scissors or a scalpel hemisect the tendon into medial and lateral halves.
14. Remove the excess bone from the table vice and place the patella bone block into the vice so that it holds it along the medial and lateral sides of the block. The proximal side of the patella should be facing the processor with the tendon going away from them. Tighten the vice so that it holds the bone block securely but does not crush it.
15. Repeat steps 10 and 11 for both plugs.
16. When the plugs are completed, remove the excess patella bone from the vice and detach the vice from the table.
17. Remove the cutter from the Jacob's chuck and place a 1.5 mm drill bit into the chuck. Tighten with the chuck key.
18. Using a saw, cut each plug to approximately 30 mm in length (no less than 25 mm)
19. Using the Arthrex clamp, place the plug into it with the end of the plug flush with the end of the clamp. Position the plug in the anterior/posterior position. Using the first guide hole nearest the flush end of the plug, drill a hole through the plug with the 1.5 mm drill bit. Turn the plug 180 degrees so that it is positioned in the medial/lateral position. Use the second guide hole from the flush end of the plug to drill a second hole through the plug.
20. Repeat step 19 for all bone plugs.
21. Using a sizing apparatus insert each bone plug into the appropriate size gauge. The entire BTB should slide completely through easily. Trim if necessary.
22. Thoroughly lavage bone plugs with sterile water or saline.

What is claimed is:

1. A bone tendon bone graft useful in orthopedic surgery comprising a tendon, said tendon comprising a first end that comprises a first attachment to a dowel-shaped first bone block and a second end that comprises a second attachment to a dowel-shaped second bone block, wherein:

said first and second attachments relate to naturally occurring attachments;

said first bone block tapers toward said first attachment, said second bone block tapers toward an end opposite to said second attachment;

said first and second bone blocks comprise a groove sufficient to accommodate a fixation screw; and said first and second bone blocks comprise a diameter of about 8 mm to about 12 mm.

2. The bone tendon bone graft of claim 1, wherein said first bone block is derived from a patella, said second bone block is derived from a tibia, and said tendon is derived from a patellar tendon.

3. The bone tendon bone graft of claim 2, wherein said groove is a radius cut extending the length of the bone block.

4. The bone block of claim 1, wherein said first bone block, second bone block, or both, comprise a thread profile positioned on the surface of said groove.

* * * * *